United States Patent
Minatelli et al.

(10) Patent No.: US 9,161,960 B2
(45) Date of Patent: *Oct. 20, 2015

(54) HORSE FEED DIETARY SUPPLEMENT COMPOSITION DERIVED FROM CHIA SEED COMPOSITION

(71) Applicant: U.S. NUTRACEUTICALS, LLC, Eustis, FL (US)

(72) Inventors: John A. Minatelli, Mount Dora, FL (US); W. Stephen Hill, Ocala, FL (US); Rudi E. Moerck, Sanford, FL (US); Uy Nguyen, Eustis, FL (US)

(73) Assignee: U.S. NUTRACEUTICALS, LLC, Eustis, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/223,043

(22) Filed: Mar. 24, 2014

(65) Prior Publication Data

US 2014/0205675 A1 Jul. 24, 2014

Related U.S. Application Data

(63) Continuation-in-part of application No. 14/103,028, filed on Dec. 11, 2013, which is a continuation-in-part of application No. 12/349,100, filed on Jan. 6, 2009, now Pat. No. 8,652,544.

(60) Provisional application No. 61/020,500, filed on Jan. 11, 2008, provisional application No. 61/020,519, filed on Jan. 11, 2008, provisional application No. 61/020,539, filed on Jan. 11, 2008, provisional application No. 61/020,583, filed on Jan. 11, 2008, provisional application No. 61/020,590, filed on Jan. 11, 2008.

(51) Int. Cl.

| | | |
|---|---|---|
| *A61K 36/537* | (2006.01) | |
| *A61K 36/00* | (2006.01) | |
| *A23K 1/18* | (2006.01) | |
| *A23K 1/16* | (2006.01) | |
| *A61K 31/201* | (2006.01) | |
| *A61K 38/16* | (2006.01) | |
| *A61K 33/00* | (2006.01) | |
| *A61K 33/42* | (2006.01) | |
| *A61K 33/06* | (2006.01) | |
| *A23L 1/30* | (2006.01) | |
| *A23L 1/36* | (2006.01) | |
| *A23L 2/02* | (2006.01) | |
| *A23L 2/52* | (2006.01) | |
| *A23G 3/48* | (2006.01) | |
| *A23L 1/0526* | (2006.01) | |
| *A23L 1/10* | (2006.01) | |
| *A23L 1/29* | (2006.01) | |

(52) U.S. Cl.
CPC ............... *A61K 36/537* (2013.01); *A23G 3/48* (2013.01); *A23K 1/164* (2013.01); *A23K 1/1806* (2013.01); *A23L 1/0526* (2013.01); *A23L 1/1041* (2013.01); *A23L 1/296* (2013.01); *A23L 1/3002* (2013.01); *A23L 1/366* (2013.01); *A23L 2/02* (2013.01); *A23L 2/52* (2013.01); *A61K 31/201* (2013.01); *A61K 33/00* (2013.01); *A61K 33/06* (2013.01); *A61K 33/42* (2013.01); *A61K 38/168* (2013.01); *A23V 2002/00* (2013.01); *A23V 2200/32* (2013.01)

(58) Field of Classification Search
IPC ............... A23L 1/296; A23V 2002/00,2200/32, A23V 2200/326; A61K 36/537
See application file for complete search history.

(56) References Cited

U.S. PATENT DOCUMENTS

| | | | |
|---|---|---|---|
| 5,332,803 A | 7/1994 | Miyazaki et al. | |
| 6,123,965 A | 9/2000 | Jacob et al. | |
| 6,827,965 B1 | 12/2004 | Fitzpatrick | |
| 8,512,765 B2 | 8/2013 | Minatelli et al. | |
| 8,574,637 B2 | 11/2013 | Minatelli et al. | |
| 8,586,104 B2 | 11/2013 | Minatelli et al. | |
| 8,652,544 B2 * | 2/2014 | Minatelli et al. | 424/746 |
| 2002/0155182 A1 | 10/2002 | Belna | |
| 2002/0168431 A1 | 11/2002 | Belna | |
| 2003/0175403 A1 | 9/2003 | Gurin | |
| 2004/0058051 A1 | 3/2004 | Yunusov et al. | |

(Continued)

FOREIGN PATENT DOCUMENTS

| | | |
|---|---|---|
| EP | 0941672 | 9/1999 |
| WO | 85/01189 | 3/1985 |

(Continued)

OTHER PUBLICATIONS

Equine Chia, Online, archived URL< https://web.archive.org/web/20120224064148/http://equinechia.com/faqs> Feb. 24, 2012, 2 pages (archived using www.archive.org).*

(Continued)

*Primary Examiner* — Patricia A Leith
(74) *Attorney, Agent, or Firm* — Allen, Dyer, Doppelt, Milbrath & Gilchrist, P.A.

(57) ABSTRACT

A horse feed dietary supplement composition increases the energy and improves the health and coat of a horse and is formed as a partially defatted seed meal composition that may be supplemented to a horse feed. The composition includes a shelf stable, partially defatted supercritical $CO_2$ fluid solvent extracted whole grain flour that is derived from *Salvia hispanica* L. whole ground seed and that is free of cyanogenic glycosides, vitamin antagonists, and gluten. The flour includes minerals, protein, insoluble fiber and from 1-25% wt/wt of about 3.0-3.3:1 mixture of ALA to LA native seed oil.

11 Claims, No Drawings

(56) References Cited

U.S. PATENT DOCUMENTS

| | | | |
|---|---|---|---|
| 2004/0137132 | A1 | 7/2004 | Nunez et al. |
| 2004/0185129 | A1* | 9/2004 | Vuksan .................. 424/776 |
| 2005/0281937 | A1 | 12/2005 | Sarna et al. |
| 2008/0095881 | A1 | 4/2008 | Ber |
| 2008/0305190 | A1 | 12/2008 | Vuksan |
| 2009/0181114 | A1* | 7/2009 | Minatelli et al. ........... 424/746 |
| 2009/0181127 | A1 | 7/2009 | Minatelli et al. |
| 2012/0027787 | A1 | 2/2012 | Minatelli et al. |

FOREIGN PATENT DOCUMENTS

| | | |
|---|---|---|
| WO | 99/62356 | 12/1999 |
| WO | 02/072119 | 9/2002 |
| WO | 2004/022725 | 3/2004 |

OTHER PUBLICATIONS

Flavel Naturestrakte: CO2 Exracts, Parfums Cosmetiques Actualities, 2007, 193, Feb./Mar. 2007, English Abstract, 1 pg.

The EFSA Journal (2005) 278, "Opinion of Scientific Panel on Dietetic Products, Nutrition and Allergies on a Request from the Commission Related to the Safety of Chia (Salvia Hispanica L.) Seed and Ground Whole Chia Seed as a Novel Food Ingredient Intended for Use in Bread," http://www.efsa.eu.int/science/nda/nda_opinions/catindex_en.html, Oct. 5, 2005, pp. 1-12.

"Supercritical Chia Seed Oil Could Become Leading Source of Omega-3 Linolenic Acid" (Online) Nov. 30, 2005, XP002515364 Retrieved from the Internet: http://www.scientistlive.com/European-Food-Scientist/Ingredients/Supercritical_Chia_Seed_Oil_could_become_leading_source_of_omega-3_linolenic_acid/14463, 4 pages.

Lin et al., "Structure of Chia Seed Polysaccharide Exudate," Carbohydrate Polymers, 1994 Elsevier Science Limited, pp. 13-18.

Weber et al., "The Nutritional and Chemical Evaluation of Chia Seeds," Ecology of Food and Nutrition, vol. 26, (1991), pp. 119-125.

Ayerza, "The Seed's Protein and Oil Content, Fatty Acid Composition, and Growing Cycle Length of a Single Genotype of Chia (Salvia hispanica L.) as Affected by Environmental Factors," Journal of Oleo Science 58, (2009), pp. 347-354.

"Valensa Introduces Tresalbio™ Salvia Hispanica Seed CO2 Extract," Oct. 9, 2006, Retrieved from the Internet: http://www.usnutra.com/resources/news/Seed-CO2.php, 2 pages.

Coates et al., "Commercial Production of Chia in Northwestern Argentina," Journal of the American Oil Chemists' Society, vol. 75, No. 10, 1998, pp. 1417-1420.

"Valensa Launches O2B™ Peroxidation Blocker Technology at Vitafoods 2006," Jun. 8, 2006, Retrieved from the Internet: http://www.usnutra.com/resources/news/Technology-Vitafoods.php, 1 page.

Surette et al., "Inhibition of Leukotriene Synthesis, Pharmacokinetics, and Tolerability of a Novel Dietary Fatty Acid Formulation in Healthy Adult Subjects," Clinical Therapeutics, vol. 25, No. 3, Mar. 2003, pp. 948-971.

Reverchon et al., "Supercritical Fluid Extraction and Fractionation of Natural Matter," Journal of Supercritical Fluids, vol. 38, No. 2, Sep. 1, 2006, pp. 146-166.

Illes et al., "Extraction of Hiprose Fruit by Supercritical CO2 and Propane," Journal of Supercritical Fluids, vol. 10, No. 3, Aug. 1, 1997, pp. 209-218.

Catchpole et al., "Extraction of Seed Oils Using Supercritical CO2 and Subcritical Propane," Proceedings of the 2nd International Meeting on High Pressure, 2001, pp. 1-13.

Taga et al., "Chia Seeds as a Source of Natural Lipid Antioxidants," Journal of the American Oil Chemists' Society, 1984 Department of Foods and Nutrition, Purdue University, West Lafayette, Indiana, vol. 61, No. 5, May 1984, pp. 928-931.

List et al., "Oxidative Stability of Seed Oils Extracted with Supercritical Carbon Dioxide," Journal of the American Oil Chemists' Society, vol. 66, No. 1, Jan. 1, 1989, pp. 98-101.

Gomez et al, "Recovery of Grape Seed Oil by Liquid and Supercritical Carbon Dioxide Extraction: A Comparison with Conventional Solvent Extraction," Chemical Engineering Journal and the Biochemical Engineering Journal, vol. 61, No. 3, Mar. 1996, pp. 227-231.

Dunford et al., "Nutritional Components of Supercritical Carbon Dioxide Extracted Wheat Germ Oil," 6th Symposium on Supercritical Fluids, Retrieved from the Internet: http://www.ensic.inpl-nancy.fr/ISASF/Docs/Versailles/Papers/PN37.pdf, 6 pages, printed Dec. 26, 2013.

Database WPI, Week 200676, Thomson Scientific, Apr. 2006, 1 pg.

Database WPI, Week 200712, Thomson Scientific, Sep. 2006, pp. 1-2.

Database GNPD, Mintel, "Slimming Tea", Apr. 2013, pp. 1-4.

Database GNPD, Mintel, "Yonsei Milk: Omega-3 Perilla Soy Milk", May 2012, pp. 1-4.

"Valensa Launches Broad New Portfolio of Perilla-based Formulations", Press Release, Mar. 2013, pp. 1-4.

Kim et al., "Supercritical carbon dioxide extraction of perilla seed oil" Korean Society of Food Science and Technology, vol. 5, No. 4, 1996, pp. 300-304.

Cho et al., "Effects of defatted safflower and perilla seed powders on lipid metabolism in ovariectomized female rats fed high cholesterol diets", Journal of the Korean Society of Food Science and Nutrition, vol. 30, No. 1, Feb. 2001, pp. 1-2.

"Perilla oil, a source of heart-healthy alpha-linolenic acid", Life Extension Magazine, Apr. 2004, pp. 1-4.

Asif, "Health effects of omega-3,6,9 fatty acids: perilla frutescens is a good example of plant oils", Oriental Pharmacy and Experimental Medicine, vol. 11, No. 1, Mar. 2011, pp. 1-9.

Asif et al., "Nutritional and functional characterisations of perilla frutescens seed oil and evaluation of its effect on gastrointestinal motility", Malaysian Journal of Pharmaceutical Sciences, 2010, pp. 1-12.

* cited by examiner

HORSE FEED DIETARY SUPPLEMENT COMPOSITION DERIVED FROM CHIA SEED COMPOSITION

RELATED APPLICATIONS

This application is a continuation-in-part application of Ser. No. 14/103,028 filed Dec. 11, 2013, which is a continuation-in-part application of Ser. No. 12/349,100 filed Jan. 6, 2009 (now U.S. Pat. No. 8,652,544), which is based upon provisional application Ser. No. 61/020,500 filed Jan. 11, 2008; and provisional application Ser. No. 61/020,519 filed Jan. 11, 2008; and provisional application Ser. No. 61/020,539 filed Jan. 11, 2008; and provisional application Ser. No. 61/020,583 filed Jan. 11, 2008; and provisional application Ser. No. 61/020,590 filed Jan. 11, 2008; the disclosures of which are incorporated herein by reference in their entirety.

FIELD OF THE INVENTION

The present invention relates to the field of chia seed products and derivatives of chia seed products and related methods and uses, for example, beverages formed from chia seeds, and more particularly, a horse feed dietary supplement composition derived from chia seed to increase the energy and improve the health and coat of a horse.

BACKGROUND OF THE INVENTION

Soybeans have been cultivated for many years throughout the world forming a food staple of extraordinary value when its seeds are further processed and refined into its component oil and flour by well-known processes. Unfortunately, soybean seed contains very low levels of polyunsaturated fatty acid esters (PUFA's) specifically removed by processes such as partial or total hydrogenation of the oil, which removes mono and polyunsaturated fatty acid esters. The resulting flour or oil, which could be partially defatted, is suitable for cooking fried foods because the resulting oil is heat stable due to its lack of polyunsaturated fatty acid esters. The resulting partially defatted flour is also processed under heat to remove the majority of the remaining fatty acid ester oils and is used extensively in bakery applications either alone or in combination with the phospholipids derived from the processing of soybeans and/or small portions of refined soy oil free of polyunsaturated fatty acid esters. Typical products include Bakers Soy Flour and Soylec sold by Archer Daniels Midland, for example.

Flax, such as flax seed, has also been cultivated and used extensively for hundreds of years as a plant based source of oils rich in the fatty acids esters of alpha-linoleic acid and linoleic acid. Unfortunately, this seed, e.g., the seed's meal, also contains significant quantities of toxic cyanogenic glycosides, Vitamin B antagonists and phytoestrogenic lignans making the seed meal undesirable for human consumption. A typical use of flax seed oil is in the production of linseed oil, which is a readily air polymerized oil and widely known for its use in oil based paints, furniture finishing applications and for the production of the flooring product commonly known as linoleum. The use of linseed oil in these applications relies on the oils lack of oxidative stability. Daily recommended human seed consumption is limited in many parts of the world due to the high level of cyanogenic glycosides found in the whole seeds. These produce toxic hydrogen cyanide once exposed to the stomach's low pH environment, certain vitamin antagonists and estrogenic lignans. Thus, flax seed or flax seed meal is generally not considered to be a good plant based source of protein or fiber due to its toxic components, antagonists and estrogenic lignans found in the seed meal.

Whey protein has also been used as a dietary supplement composition. It is the name for a collection of globular protein that can be isolated from whey, a by-product of cheese manufactured from cow's milk. It is typically a mixture of beta-lactoglobulin (~65%), alpha-lactalbumin (~25%), and serum albumin (~8%), which are soluble in their native forms, independent of pH. Whey has the highest Biological Value (BV) of any known protein.

The protein fraction in Whey (approximately 10% of the total dry solids within Whey) comprises four major protein fractions and six minor protein fractions. The major protein fractions in whey are beta-lactoglobulin, alpha-lactalbumin, bovine serum albumin and immunoglobulins. Each of these components have important disease-fighting effects. In addition, whey protein is easily digestible.

Whey protein can be denatured by heat. High heat (like the sustained high temperatures above 72 degrees Celsius (160 degrees Fahrenheit) associated with the pasteurization process) denatures whey proteins, destroying some bioactive compounds, such as the amino acid cysteine. While native whey protein does not aggregate upon renneting or acidification of milk, denaturing the whey protein triggers hydrophobic interactions with other proteins, and the formation of disulfide bonds between whey proteins and casein micelles, leading to aggregation with other milk proteins at low pH.

Whey protein typically comes in three major forms: concentrate, isolate and hydrolysate. Whey protein concentrates contain a low level of fat and cholesterol but generally have higher levels of bioactive compounds, and carbohydrates in the form of lactose—they are 29%-89% protein by weight. Isolates are processed to remove the fat, and lactose, but are usually lower in bioactive compounds as well—they are 90%+protein by weight. Both of these types are mild to slightly milky in taste. Hydrolysates are predigested, partially hydrolyzed whey proteins which consequently are more easily absorbed, but their cost is generally higher. Whey protein hydrolysate also tends to taste quite different than other forms of whey protein, usually in a way that many find undesirable but can be masked when used in beverages.

More than other protein supplements, whey protein powder is commonly used by bodybuilders and other athletes to accelerate muscle development and aid in recovery. Some individuals with suppressed or otherwise abnormal immune systems or degenerative diseases use undenatured bioactive whey proteins to increase their antioxidant levels. Undenatured whey proteins are a good source of cysteine, a conditionally essential amino acid which is the rate limiting factor for the body's production of glutathione, an important antioxidant.

Examples of commercial whey proteins include those available in most health food stores and supermarket health sections. They typically are formed of isolate/concentrate or isolate/concentrate/hydrolysate mixtures and are usually flavored so they can be mixed with water or milk and consumed as a drink or shake. However, whey protein contains little or no soluble or insoluble fiber and no PUFA content. Other diet avenues are desirable.

*Salvia hispanica* L. is a known, yet ancient, cultivated seed that was consumed by the Aztec and Mayan cultures where it was a highly prized food staple. In fact, their well balanced diet consisted primarily of corn, beans, amaranth and chia seed. In addition, chia seed is a critical component of the well known "Chia Pet" due to the seed's ability to readily absorb and retain moisture, its high level of germination and its sticky muco-polysaccharide outer seed coating.

In addition to consuming the whole seed, these cultures also prepared a ready-to-drink, non-shelf stable (thus unstable) beverage by mixing chia seed with various fruit juices including, for example, lime juice in a ratio of approximately 1:12 to 1:30 seed to juice wt/wt ratios with or without the addition of sugar. The product, which is still made today locally in Central and South America, is commonly referred to as "Chia Fresca". It is unstable, however.

*Salvia hispanica* L. is known to contain high natural levels of the essential polyunsaturated fatty acid triglycerides of alpha-linolenic acid ("ALA") an "omega-3" fatty acid and linoleic acid ("LA"), an essential "omega-6" fatty acid, in a unique ratio of approximately 3.3:1. The seed provides approximately 33% seed oil, 21% protein, 41% total dietary fiber and high levels of minerals such as calcium, iron, magnesium and phosphorus. The total composition of chia seed is well known to those skilled in the art. In addition, this seed, unlike flax seed, contains no gluten, cyanogenic glycosides, lignans or vitamin B antagonists. Therefore chia seed is an excellent source of essential polyunsaturated fatty acids, protein, fiber and minerals.

Some hundreds of years ago, the seed crop was destroyed during the Spanish conquest of the Central American cultures to interrupt the food supply. Only in recent years have agronomists successfully re-cultivated this re-emerging seed for use in "Chia Pets" and more recently as a viable source of the plant-based essential fatty acids, e.g., ALA and LA. The seed has unique benefits of high levels of the essential fatty acid esters of ALA and LA, protein, both soluble and insoluble dietary fiber, and high levels of calcium, potassium, magnesium and phosphorus. An advantage is the seed typically contains no cyanogenic glycosides, Vitamin B antagonists or the phytoestrogenic lignans found in flax seed. This makes the *Salvia Hispanica* L. seed an excellent and relatively new source of plant based ALA and LA. Many unique properties of this seed are disclosed in U.S. Patent Publication Nos. 2002/0155182, 2004/0185129, and 2004/0137132, and U.S. Pat. Nos. 5,332,803 and 6,123,965, the disclosures which are hereby incorporated by reference in their entirety.

Some commercial operators hydrate and separate seed coat polysaccharide from water pre-soaked seeds to derive a separated seed gel coat useful in the preparation of gel enhanced beverages and later apply the whole seed for the treatment and prevention of human diseases. The operators also produce expeller pressed flour from *Salvia hispanica* L seed, which is used either alone or admixed with other grain or legume seed flours, meat based seasonings, vegetable based pastes, diary-based products and the like.

It is well known that solvent based or expeller press based extraction of *Salvia hispanica* L. seed leads to the isolation of seed oil containing high levels of the polyunsaturated essential fatty acid esters ALA and LA as well as other oils such as the saturated fatty acid esters of palmitic and stearic acids and the monounsaturated fatty acid ester of oleic at levels as high as 30% of the seed weight. These oils, which are very rich in the polyunsaturated triglycerides of ALA and LA, are extremely unstable once exposed to any oxidative potential, including the oxygen found in air. Therefore, it has been found that exposure of the solvent extracted seed oil to air results in rapid oxidative degradation of the oil and accompanying oil rancidity, not unlike the oils derived from flax seed. Thus, the native oils that are extracted from *Salvia hispanica* L. exhibit very poor shelf life and present a significant challenge for shelf life stabilization. Therefore, the whole grain seed has been used extensively to date rather than its component parts to deliver the health benefits of the seed in human as well as animal diets. For example, in the Americas, *Salvia hispanica* L. seed has for a long time been first pre-soaked in water to absorb up to nine to twelve times its weight in water to which various fruit juices have been added to produce a product known as "Chia Fresca" for immediate consumption.

Other details concerning the use of chia are found in the Opinion of Scientific Panel on Dietetic Products, Nutrition and Allergies on a request from the Commission related to the safety of chia (*Salvia hispanica* L.) seed and ground whole chia seed as a novel food ingredient intended for use in bread, e.g., the EFSA Journal 278, 1-2; (2005); http://www.efsa.eu.int/science/nda/nda opinions/catindex en.html the disclosure which is hereby incorporated by reference in its entirety.

The incorporated by reference parent and grandparent '028 and '100 applications address some of the technical shortcomings indicated above and disclose a shelf stable, partially defatted supercritical CO2 fluid solvent extracted whole grain flour derived from *salvia hispanica* L. whole ground seed that is free of cyanogenic glycocides, vitamin antagonists and gluten. The flour includes minerals and from 1-25% wt/wt of about 3.0-3.3:1 mixture of ALA to LA native seed oil, protein, and insoluble fiber. In one example, it contains fructo-oli-cosaccharides and exhibits pH dependent thixotropic properties when mixed with water. This seed meal composition has a high percentage of protein, fiber and a high level of omega-3 alpha-linolenic acid (ALA).

It is known that horse composition, fatty acid dietary supplements are often added to horse feed to add weight to the horse, add energy, improve the hair coat, decrease muscle spasms minimize the tying-up syndrome (equine rhabdomyolysis), and treat polysacharride storage (PSSM). Many of these horse composition, fatty acid dietary supplements contain different fats or proteins that are not desired as a feed for the horses because the horses reject the supplement as unpalatable. In certain instances, these supplements may have a negative impact on the horse's diet, metabolism, mane and physiology.

It is therefore desirable to provide a horse feed dietary supplement composition such as added by top dressing the horse feed, which increases the energy and improves the health and coat of a horse and will be an acceptable diet to the horse as a supplement to grain or hay.

SUMMARY OF THE INVENTION

A horse feed dietary supplement composition increases the energy and improves the health and coat of a horse and is formed as a partially defatted seed meal composition that may be supplemented to a horse feed. The composition includes a shelf stable, partially defatted supercritical $CO_2$ fluid solvent extracted whole grain flour that is derived from *Salvia hispanica* L. whole ground seed and that is free of cyanogenic glycosides, vitamin antagonists, and gluten. The flour includes minerals, protein, insoluble fiber and from 1-25% wt/wt of about 3.0-3.3:1 mixture of ALA to LA native seed oil.

In one example, the horse feed is top dressed with the partially defatted seed meal composition and supplemented in an amount from about 0.5 to about 1.5% by weight of the horse feed fed to the horse on a daily basis, corresponding in one example to about 2 ounces of the partially defatted seed meal composition top dressed to the horse feed, once in the morning and once in the evening.

In another example, the flour is formed as 30-40% insoluble fiber and in another example, about 48-60% insoluble fiber. In yet another example, the flour is about 25-35% by weight of protein, and in an example, 30% by weight of protein. The flour may include 5-8% of the about 3.0-3.3:1 mixture of ALA to LA native seed oil. In another example, the flour exhibits pH dependent thixotropic properties when mixed with water. The flour may include fructo-oligosaccharides, which may be about 2-3%.

DETAILED DESCRIPTION OF THE PREFERRED EMBODIMENTS

The present invention will now be described more fully hereinafter. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The partially defatted seed meal composition may be used as a horse feed dietary supplement composition that aids in increasing the energy and improving the health and coat of a horse. Not only has it been found that this horse feed dietary supplement composition is not rejected as a dietary feed by the horse, but it improves energy and digestion for the horse, increases insulin resistance, increases joint and muscle flexibility, and increases the hoof growth and the condition of the coat, mane and tail. There now follows the description as contained in the parent and grandparent '028 and '100 applications as set forth in those incorporated by reference disclosures, followed by greater details of the horse feed dietary supplement composition and method used to increase the energy and improve the health and coat of a horse using that composition.

In accordance with non-limiting aspects, it has been found that partially defatted whole grain flour, resulting from a partial solvent based extraction of pre-milled *Salvia hispanica* L. seed, though containing significant quantities of polyunsaturated oils, including essential polyunsaturated fatty acid esters of ALA and LA, is stable. This resulting flour's stability serves as an excellent, stable delivery platform for the essential fatty acid esters of ALA, LA, protein, soluble and insoluble fiber, minerals such as calcium, potassium, magnesium and phosphorus, and both lipophilic and hydrophilic additives, which is free of cyanogenic glycosides, vitamin B antagonists, lignin and gluten. The resulting product can be used as a food ingredient in a beverage and as a dietary supplement ingredient to various foods, including the horse feed dietary supplement composition. It can provide beneficial results in enhancing gastrointestinal regularity and heart health.

The resulting partially defatted whole grain flour, despite its unique composition, exhibits an ability to reabsorb large quantities of lipophilic as well as hydrophilic additives while exhibiting a pH dependent thixotropic effect in aqueous environments. The flour as a composition is a novel and inventive food or beverage or dietary supplement ingredient delivery vehicle for lipophilic and hydrophilic additives in the presence of protein, fiber, various levels of the essential fatty acid esters of ALA and LA and minerals that are free of cyanogenic glycosides, vitamin B antagonists, lignin and gluten.

In accordance with a non-limiting aspect, the composition of matter enhances the protein, fiber, mineral content and pH controlled viscosity of beverages and their liquid concentrates, dried beverage pre-mixes including protein shakes and fruit smoothies, ready-to-drink beverages, beverage pre-mixes, frozen fruit concentrates, alcoholic beverage dry pre-mixes and concentrates, meal replacement beverages, drinkable dairy and non-dairy yogurts, gravies and dry gravy pre-mixes, and ready to drink and dried pre-mixed infant formulas. The composition of matter can be formed from wholly or partially defatted *Salvia hispanica* L. whole ground grain meal obtained by supercritical fluid extraction of *Salvia hispanica* L. ground seeds.

In one non-limiting example, supercritical $CO_2$ fluid solvent extraction of pre-ground *Salvia hispanica* L. seed alone or in the presence of a mixture of hydrophilic and/or lipophilic antioxidants is used to obtain a wholly or partially defatted whole grain meal containing variable amounts of the stabilized essential polyunsaturated fatty acid esters of ALA and LA (omega-3 and omega-6 esters) and optionally containing either non-native *Salvia hispanica* L. derived lipophilic or hydrophilic additives. It is useful in a number of food applications.

The resulting seed meal provides a unique blend of protein, insoluble and soluble fiber, and variable amounts of the essential fatty acid triglycerides of alpha-linolenic acid (omega-3, "ALA") and linoleic acid (omega-6, "LA") in a desirable and unique ratio of approximately 3.3:1.0 ALA to LA, along with high levels of calcium, potassium, magnesium and phosphorus that is free of cyanogenic glycosides, lignans vitamin B antagonists and gluten.

The resulting flour can be incorporated into beverages, dry beverage pre-mixes, liquid or frozen beverage concentrates and the like with the added feature of pH controlled viscosity by either the amount of *Salvia hispanica* L. derived meal that is added and/or by optionally lowering the pH with an acidulant to improve further the viscosity of the resulting beverage.

Example 1

The composition of matter in this example is formed from a stable, partially or wholly defatted whole grain meal derived from *Salvia hispanica* L. whole ground seed using a suitable solvent such as supercritical carbon dioxide. It is rich in minerals. In one aspect, it contains about a 3.0 to about 3.3:1 mixture of essential fatty acid esters of ALA and LA (Polyunsaturated fatty acids "PUFA's"), and is optionally admixed with lipophilic or hydrophilic additives, such that the total lipophilic content is between from about 0 to about 25 wt/wt percent of the resulting meal weight and the resulting hydrophilic content is between about 0 and about 10 wt/wt percent of the resulting meal, protein, soluble and insoluble fiber and fructo-oligosaccarides and free of cyanogenic glycosides, vitamin B antagonists, lignans and gluten. It can be used to prepare a beverage, beverage concentrate or dried beverage pre-mix ingredient.

In one aspect, the composition as formed is added to a beverage, liquid concentrate, or dried beverage pre-mixes. The composition can be used for prepared beverages, their liquid concentrates, and dried pre-mixes, including protein shakes, fruit smoothies, ready to drink beverages, dry beverage pre-mixes, frozen fruit concentrates, aqueous alcoholic beverage pre-mixes, concentrates or their dried pre-mixes, vitamin, carbohydrate and protein fortified meal replacement beverages, drinkable dairy and non-dairy yogurts, gravies and dry gravy pre-mixes, and ready to drink and dried pre-mixed infant formulas. The composition with such uses can include added lipophilic additives and added hydrophilic additives. The pH range can be adjusted with the addition of one or more acidulants to bring the pH of the final product to a pH of from about 3 to about 6.5 to further thicken the resulting beverage.

The composition of matter as described and used can be prepared in a pasteurized beverage form. In its use, it is shelf stable and contains sterilized whole seed from *Salvia hispanica* L. in an admixture with a wide range of liquid beverage components, including but not limited to, for example, fruit derived juices, water or natural or artificially flavored water such as colas, coffees, teas and the like. It can contain a sweetener such as sucrose, fructose corn syrup or an artificial sweetener. It can also contain preservatives such as sodium benzoate and such other additives common to beverage formulations. The resulting beverage exhibits a pH dependent viscosity. The resulting beverage is also rich in fiber and is particularly useful for maintaining good gastrointestinal system regularity in a convenient and tasty beverage form while delivering heart healthy polyunsaturated fatty acids, protein and minerals.

Method of Manufacturing

In a non-limiting example of a method of manufacturing, clean chia seed is in a first step sterilized to prevent unwanted germination. The sterilization of seed can be accomplished by flash steam treatment of the seed, by radiation and similar processes. Following sterilization, the seed is then pre-soaked in water in one example at a ratio of from about 1:9 to about 1:30 wt/wt seed to water for a period of time to effect adsorption of the water by the seed and form a gel-like outer coating on each seed. Typical time required for such outer gel coat formation is typically from between about 3 to about 24 hours at about 5 to about 25 Degrees Centigrade depending on the desired beverage characteristics. The pre-soaked seeds are added, for example, to a fruit juice optionally containing one or more sweeteners, and/or preservatives to prepare the final beverage for pasteurization with a seed-to-juice ratio of from about 1:12 to about 1:50 wt/wt in this example. The beverage can be added to pre-washed containers and pasteurized to form the final shelf stable beverage.

Optionally in yet another aspect, the beverage may be prepared by adding whole seed directly to the other beverage ingredients dissolved in water artificially or naturally flavored water or fruit juice, and optionally stirring from about 1 to about 24 hours and between about 5 to about 25 Degrees Centigrade to effect gel coat formation of the seed and associated pH dependent beverage thickening. The resulting beverage mixture is conventionally or flash pasteurized to prevent post bottling seed germination and enhance shelf life.

Example 2

In a non-limiting example, the composition of matter is in a shelf stable pasteurized beverage form and contains sterilized whole seed from *Salvia hispanica* L. in an admixture with a wide range of liquid beverage components, including but not limited to, fruit derived juices, water or naturally or artificially flavored water such as colas, coffees, teas and the like. It can contain a sweetener such as sucrose, fructose corn syrup or an artificial sweetener, and contain preservatives such as sodium benzoate and such other additives common to beverage formulations. The resulting beverage exhibits a pH dependent viscosity requiring no additional thickening agents.

The beverage can be enriched in protein, polyunsaturated essential fatty acid triglycerides, minerals and rich in fiber particularly useful for maintaining good gastrointestinal system regularity in a convenient and tasty beverage form while delivering heart healthy polyunsaturated fatty acids, protein and minerals requiring no additional thickening agents. It can be useful for the control of hunger via satiety requiring no additional thickening agents to effect such satiety.

A similar method of manufacturing as described relative to that described in Example 1 can be used. As noted before, supercritical CO2 fluid solvent extraction can be used for *Salvia hispanica* L. seed alone or in the presence of a mixture of natural hydrophilic and lipophilic antioxidants. Stabilized, partially defatted whole grain flour containing variable amounts of the unstable essential polyunsaturated fatty acid esters of ALA and LA (omega-3 and omega-6 esters) is prepared from antioxidant pretreated, pre-ground seeds of *Salvia hispanica* L. The resulting gluten free flour provides a unique blend of protein, insoluble and soluble fiber. The essential fatty acid triglycerides of alpha-linolenic acid (omega-3, "ALA") and linoleic acid (omega-6, "LA") are in a desirable and unique ratio of approximately 3.3:1.0 ALA to LA, along with high levels of calcium, potassium, magnesium and phosphorus. The total oil content of the resulting flour can vary between about 1 and about 25 percent wt/wt of the original seed oil content of approximately 33% wt/wt.

The resulting flour can be incorporated into beverages, dietary supplement bars, nutritional bars, baked goods, confectionary fillings, icings, processed meats, peanut butter, jellies and the like as delivery vehicle for quantities of the essential fatty acid esters of ALA and LA, protein, soluble and insoluble fiber, and minerals depending on the amount of ALA and LA retained in the partially defatted flour and the amount of the flour employed in the end user formulation.

In addition, the resulting partially defatted whole grain flour is capable of re-absorbing and stabilizing relatively large quantities of other lipophilic compounds providing a convenient vehicle for delivery of these compounds in addition to ALA, LA, protein, insoluble fiber and minerals as an ingredient in food, beverage and dietary supplement based formulations. The partially defatted whole grain flour can reabsorb lipophilic compounds of from about 1 to about 25 percent of the weight of the partially defatted whole grain flour, depending on the level of native seed oil remaining in the solvent extracted, whole grain flour.

The resulting flour also exhibits unique pH dependent thixotropic properties when added to aqueous based formulations such as beverages, including protein-based smoothies. It also provides a unique method or process for mitigating the undesirable free water associated with nutritional and dietary bar production, while providing ALA, LA, protein, soluble and insoluble fiber and minerals to such formulations and providing other lipophilic compounds depending on the composition of the flour employed.

Example 3

The composition of matter, in accordance with another non-limiting aspect, is formed of a stable, partially defatted whole grain flour derived from *Salvia hispanica* L. whole ground seed, using a suitable solvent, and is rich in minerals and contains from about 1 to about 25 percent wt/wt of a 3.0 to 3.3:1 mixture of the essential fatty acid esters of ALA and LA, approximately 30% wt/wt protein, approximately 30-40% insoluble fiber and about 2-3% of fructo-oligosaccarides, and is also free of cyanogenic glycosides, vitamin B antagonists and gluten. It is used as a delivery vehicle for the introduction of ALA, LA, protein, soluble and insoluble protein and minerals to foods, beverages and dietary supplements. It can be used either alone or in combination with other additives to enrich the healthiness or functionality of the resulting products.

In one aspect, the composition as a product is used with a beverage or protein shake "smoothie" or nutritional bar or dietary supplement bar enriched in protein, fiber, minerals and a controlled portion of ALA and LA. The product also can be used with a confectionary filling enriched in protein, fiber, minerals and a controlled portion of ALA and LA. It can also be used with an icing or processed meat or peanut butter or jelly enriched in protein, fiber, minerals and a controlled portion of ALA and LA.

The product can also be used with a chocolate, pectin or gelatin based confectionary or dietary supplement whose inner filling, outer shell or integrated composition is enriched in protein, fiber, minerals and a controlled portion of ALA and LA. It can be used with a pasta enriched in protein, fiber, minerals and a controlled portion of ALA and LA.

In another aspect, the composition of matter is a stable, partially defatted whole grain flour derived from *Salvia hispanica* L. whole ground seed, using a suitable solvent, rich in minerals, containing in combination, from about 1 to about 25 percent wt/wt of about a 3.0 to 3.3:1 mixture of the essential fatty acids ALA to LA, and absorbed lipophilic additive(s), approximately 30% wt/wt protein, approximately 30-40% of soluble and insoluble fiber and about 2-3% of fruto-oligosaccarides, which are free of cyanogenic glycosides, vitamin antagonists and gluten. It is used as a delivery vehicle for the introduction of ALA, LA, protein, soluble and insoluble protein, minerals and lipophilic additives to foods, beverages and dietary supplements and used either alone or in combination with other additives to enhance the healthiness or functionality of the resulting products.

In another aspect, the composition of matter is a stable, partially defatted whole grain flour derived from *Salvia hispanica* L. whole ground seed, using a suitable solvent, rich in minerals, containing, in combination, a total of from about 1 to about 25 percent wt/wt of about a 3.0 to 3.3:1 mixture of the essential fatty acids ALA to LA, and an absorbed hydrophilic additive, approximately 30% wt/wt protein, approximately 30-40% of soluble and insoluble fiber and about 2 to about 3 percent of fructo-oligosaccharides and free of cyanogenic glycosides, vitamin antagonists and gluten, used as a delivery vehicle for the introduction of ALA, LA, protein, soluble and insoluble protein, minerals and lipophilic additives to foods, beverages and dietary supplements. It is used either alone or in combination with other additives to enhance the healthiness or functionality of the resulting products.

As noted before, using the super-critical $CO_2$ fluid extraction method of preparation, the resulting flour can be incorporated into beverages, dietary supplement bars, nutritional bars, baked goods, confectionary fillings, icings, processed meats, peanut butter, jellies and the like as a partially soluble delivery vehicle for heart healthy quantities of the essential fatty acids ALA and LA, protein and soluble and insoluble fiber depending on the amount employed in the end user formulation.

Example 4

In another non-limiting example, the composition of matter is formed as a stable, partially defatted whole grain flour derived from *Salvia hispanica* L. whole ground seed using a suitable solvent which is free of cyanogenic glycosides, vitamin antagonists, gluten, rich in minerals and containing from about 1 to about 25 percent wt/wt of about a 3.0 to 3.3:1 mixture of ALA to LA native seed oil, approximately 30% wt/wt protein and approximately 30-40% insoluble fiber and 2-3% of fruto-oligosaccarides.

The composition exhibits pH dependent thixotropic properties when admixed in water bearing compositions. The composition can be formed as partially defatted whole grain flour derived from *Salvia hispanica* L. whole ground seed containing from about 1 to about 25 percent wt/wt of a mixture containing ALA and LA fatty acid esters, protein, insoluble fiber, minerals and other lipophilic additives such as DHA or EPA fatty acid esters or other health or functional lipophilic compounds. In another aspect, it can include lipophilic compounds reabsorbed into the flour including one of at least rosemary oil, tocopherols, tocotrienols, carotenoids, seed oils, lipophilic solvent extracted botanical oils, lipophilic food flavorings or other health or functional hydrophilic compounds.

In another aspect, the composition can include hydrophilic additives re-absorbed into the flour such as, for example, hydrophilic solvent extracts of botanicals, green tea extract, grape seed extract, ascorbic acid, caffeine, mono and/or polysaccharides, gums, phospholipids, biopolymers, hydrophilic food flavorings or other health or functional hydrophilic compounds. In yet another aspect, the composition has been pretreated with a suitable proteolytic enzyme or plurality of enzymes to produce a novel probiotic mixture rich in essential amino acids. It can also be pretreated with a suitable cellulase or amylase enzyme or enzymes, which degrades the soluble and insoluble fiber to produce a novel probiotic mixture rich in digestible monosaccharide and oligosaccharide units in another example.

In yet another method example, supercritical $CO_2$ fluid extraction is used on *Salvia hispanica* L. seed alone or in the presence of a mixture of naturally available hydrophilic and lipophilic antioxidants. It is possible to prepare a completely defatted whole grain flour from pretreated pre-ground seeds of *Salvia hispanica* L. The resulting gluten free flour provides a unique blend of protein, insoluble and soluble fiber, along with high levels of the minerals calcium, potassium, magnesium and phosphorus.

The resulting flour can also be incorporated into beverages, dietary supplement bars, nutritional bars, baked goods, confectionary fillings, icings, processed meats, peanut butter, jellies, bakery goods and the like as a delivery vehicle for protein, soluble and insoluble fiber and minerals or as a dessicant in food applications where excess water creates a formulation problem.

In addition, the resulting defatted whole grain flour is capable of re-absorbing and stabilizing relatively large quantities of other lipophilic compounds providing a convenient vehicle for delivery of these compounds in addition to protein soluble and insoluble fiber and minerals as an ingredient in food, beverage and dietary supplement based formulations. The defatted whole grain flour can re-absorb lipophilic compounds of about 1 to about 25 percent of the weight of the defatted whole grain flour.

The resulting defatted whole grain flour exhibits the ability to reabsorb large quantities of lipophilic as well as hydrophilic additives, while exhibiting a pH dependent thixotropic effect when subjected to aqueous environments. The defatted flour is a novel food, beverage or dietary supplement ingredient delivery vehicle for lipophilic and hydrophilic additives in the presence of protein, fiber and minerals that are free of cyanogenic glycosides, vitamin B antagonists, lignin and gluten.

Example 5

In another non-limiting example, the composition of matter can be formed as a stable, completely defatted whole grain flour derived from *Salvia hispanica* L. whole ground seed using a suitable solvent which is free of cyanogenic glycosides, vitamin antagonists, gluten, and contains minerals, approximately 30% wt/wt protein, approximately 30-40% insoluble fiber and 2-3% of fructo-oligosaccarides.

It exhibits pH dependent thixotropic properties when admixed in water bearing compositions. Lipophilic compounds can be reabsorbed into the flour such as, for example, rosemary oil, tocopherols, tocotrienols, carotenoids, seed oils, lipophilic solvent extracted botanical oils, lipophilic food flavorings, polyunsaturated fatty acid esters or other health or functional hydrophilic compounds. It can be admixed with hydrophilic additives re-absorbed into the flour such as, for example, hydrophilic solvent extracts of botanicals, green tea extract, grape seed extract, ascorbic acid, caffeine, mono and or polysaccharides, gums, phospholipids, biopolymers, hydrophilic food flavorings or other health or functional hydrophilic compounds.

In yet another aspect, the composition can be pretreated with a suitable proteolytic enzyme or plurality of enzymes to produce a probiotic mixture rich in essential amino acids. It can be pretreated with a suitable enzyme or enzymes, which degrade the soluble and insoluble fiber to produce a probiotic mixture rich in digestible monosaccharide and oligosaccharide units.

In yet another aspect, the composition of matter is formed as a stable, defatted whole grain flour derived from Salvia hispanica L. whole ground seed, using a suitable solvent, rich in minerals and approximately 30% wt/wt protein, approximately 30-40% insoluble fiber and about 2-3% of fructo-oligosaccharides free of cyanogenic glycosides with vitamin B antagonists and gluten as a delivery vehicle for the introduction of protein, soluble and insoluble protein and minerals to foods, beverages and dietary supplements, either alone or in combination with other additives, to enrich the healthiness or functionality of the resulting products. The composition of matter can be formed as a product in beverage or protein shake "smoothie" form and enriched in protein, fiber, and minerals. The final product can be a nutritional bar or a dietary supplement bar enriched in protein, fiber, and minerals. It can also be used with a confectionary filling or peanut butter or jelly enriched in protein, fiber, minerals or an icing or processed meat enriched in protein, fiber, minerals and a controlled portion of ALA and LA. In another example, it can also be used with a product such as a chocolate, pectin or gelatin based confectionary or dietary supplement whose inner filling, outer shell or integrated composition is enriched in protein, fiber, and minerals. The product can also be used with a pasta enriched in protein, fiber, and minerals.

Further aspects have been developed in the seed preparation, supercritical CO2 fluid extraction, and fractionation to form the product to better meet consumer expectations. The general parameters of the raw material specification for the chia seed and the product specification for the ChiaMax™ flour are still applicable and are explained below.

The raw material specification for the chia seed and the product specification for the low fat whole grain ChiaMax™ omega-3 product are set forth as non-limiting examples. Both specifications can vary, of course. The final product after seed preparation, extraction and fractionation is sold under the tradename ChiaMax™.

TABLE I

| Raw Material Specification for Chia Seed | | |
|---|---|---|
| Chia Seed | Chia (Salvia hispanica L.) seed | |
| Raw Material Country of Origin: | Australia, Mexico, Bolivia, Nicaragua, Guatemala, India or Argentina | |
| Physical | | |
| Appearance | Oval [2 mm × 1.5 mm] with smooth, shiny grayish black veined coloration | |
| Foreign Organic Matter | <1% | USP <561> |
| Heavy Metals | <10 ppm | ICP-MS |

TABLE I-continued

| Raw Material Specification for Chia Seed | | |
|---|---|---|
| Chemical | | |
| Pesticide Residues | Negative screen | |
| Total Lipids | >28% | Hexane Soxhlet |
| Fatty Acid Profile | | GC |
| Palmitic acid | 4...8% | |
| Stearic acid | 1...5% | |
| Oleic acid | 4...10% | |
| Linoleic acid | 14...23% | |
| α-Linolenic acid | 50...65% | |
| Peroxide Value | <10 meq/g | |
| Microbiological | USP <61> | |
| Total Plate Count | max. $10^5$/g | |
| Yeast/Mold | max. $10^2$/g | |
| E. coli/Coliforms | <10/g | |
| Salmonella | Negative | |

TABLE II

| Improved Product Specification for ChiaMax™ ChiaMax™ Omega-3 Low Fat Whole Grain CG | | |
|---|---|---|
| Ingredient: | Chia (Salvia hispanica L.) seed (partially defatted with supercritical $CO_2$); also known as Spanish Sage | |
| Chia Seed Country of Origin: | Mexico, Bolivia, Australia, India or Argentina Kosher certified by KSA | |
| Physical | | |
| Appearance | Brown-beige coarse powder | |
| Taste | Characteristic, mild nutty | |
| Solubility | Forms viscous suspension in water | |
| Bulk Density | 0.2-0.3 g/mL | |
| Chemical | | |
| Fat | 5-8% | Hexane Soxhlet |
| Omega-3 (ALA) | 2.8-4.5 g/100 g (as-is) | GC-FAME |
| Protein | 25-35% | |
| Fiber | 48-60% | |
| Pesticides | No detectable pesticide residues (>RL) on CDFA or similar seed raw material used to manufacture product | |
| Microbiological | USP <61> | |
| Total Plate Count | max. $10^4$/g | |
| Yeast/Mold | max. $10^3$/g | |
| E. coli/Coliforms | <10/g | |

Attempted extraction of Saliva hispanica L. un-milled seed, using supercritical $CO_2$ even at extraordinarily high pressures of 1000 bar or hexane solvent at atmospheric pressures, yields very little, if any, seed oil, in this process. Therefore, the seed is milled prior to extraction. The extent of the milling, as measured by particle size distribution, is advantageous to an extraction process in accordance with a non-limiting aspect since the higher the surface area, the higher will be the efficiency and completeness of the extraction process by either organic solvent based or supercritical fluid based processes. In addition, it is often advantageous to mill the seed in a blanket of inert gas such as nitrogen to prevent per-oxidative processes from taking place that would otherwise be initiated in the presence of air or oxygen and light.

To make some varieties of chia seed oil, Salvia Hispanica L. whole seed has been commutated in a standard knife or hammer mill or roller milled, preferably under a cold nitrogen atmosphere, to produce cracked seed biomass. This biomass has been treated with one or more hydrophilic and/or lipophilic antioxidants and then subject to CO2 extraction.

An improved manufacturing procedure for the shelf-stable, partially defatted supercritical CO2 fluid solvent extracted whole grain flour such as described in Table II above is now set forth.

Overview

Commercially available dried ripe Chia (*Salvia hispanica*) seed is flaked and extracted with supercritical carbon dioxide to remove a substantial portion of the lipids. This defatted seed is marketed as a dietary supplement and functional food ingredient. The entire facility is designed to operate under food GMP (Good Manufacturing Practice).

Example Manufacturing Procedure

1. Dried, ripe whole Chia seeds are received and analyzed for fatty acids. Intact seeds are typically impermeable to solvents and require cracking prior to oil extraction.
2. Seeds are flake cracked in a roller mill fitted with 10 inch diameter, 6 inch wide smooth steel rolls with a 0.005-0.010 inch gap. Rolls spin with a differential rotational speed of 1.5:1.
3. Rosemary extract containing 20-40% w/w carnosic acid antioxidant is combined with the cracked seed at a rate of approximately 0.3 grams carnosic acid per 1 kg chia seed. The carnosic acid provides oxidative stability to the extracted chia oil.
4. Stainless steel extraction baskets with upper and lower steel mesh screens and 150 liter capacity are filled with approximately 60 kg cracked chia seeds and placed into a high pressure extraction vessel.
5. Clean food-grade carbon dioxide (without chemical co-solvents or entrainers) in the supercritical state (200-700 bar; 40-80° C.) is passed through the extraction baskets to "load" chia seed lipids and rosemary carnosic acid into the $CO_2$.
6. The loaded carbon dioxide exits the extraction vessel and passes through an expansion valve towards a first separation vessel under lower pressure and temperature (100-220 bar; 35-60° C.) to reduce the solubility of lipids in the $CO_2$. The majority of chia oil precipitates and is separated from the carbon dioxide.
7. The carbon dioxide continues from the first separation vessel through an expansion value towards a second separation vessel under lower pressure and temperature (30-70 bar; 15-30° C.) so that the CO2 is transformed into the gas state. The remainder of chia oil and water accumulated from extraction precipitates into this second vessel.
8. Carbon dioxide is recovered and recycled. For each kilogram of chia seed, 30-40 kg of carbon dioxide is passed through the seed to extract the lipids.
9. The extraction vessel is depressurized and the partially defatted chia seed is removed from the extraction basket to complete the extraction cycle.
10. The ChiaMax™ final product and the partially defatted flour is packaged into airtight plastic-lined boxes or totes. Samples are analyzed for content of: fat, protein, fiber, ash and microbiological profile.

An improved form of the composition has been used as a horse feed. Although the described below test results were used with horses, the composition may be used with other animals to improve the coat, mane, and tail condition of the horse or other animal and improve the horse's or other animal's hoof growth, digestion, insulin resistance and joint/muscle flexibility.

Fatty acids such as ALA and LA and other components naturally occur in food stuffs, including forage used with horse feed. High-fat diets are sometimes applied as a horse feed in order to increase the horse's energy and weight. The energy from fat is about 2.25 times more than an equal amount of carbohydrate or protein. In an example, one pound of fat may be equal in energy to about 3 pounds of oats or 2.5 pounds of corn. Feeding a horse too many pounds of grain, however, such as up to 5 pounds of grain per feeding, may disrupt the microbial balance in the horse's hind gut because some grain escapes digestion and passes into the hind gut and leads to colic or laminitis. Certain types of fats may be added to horse feed to improve the hair coat. It is believed that the fat secreted from glands in the horse skin coats the hair shaft, giving the hair shaft a coating of different fatty acids that protect the hair from the effects of sun and weather. As a result, the horse's mane coat looks shinier and it is most probably stronger. Also, the fatty acids in this horse dietary supplement composition may reduce symptoms of polysaccharide storage myopathy (PSSM) and reduce symptoms related to "tying up." The fatty acids also may place greater weight on the horse, making the horse healthier, adding energy to the horse, improving its hair coat, and increasing its amenability for training.

Most common fatty acids are the omega-3 and omega-6 fatty acids and both are essential. Omega-3 fatty acids are preferred and are considered less inflammatory than the omega-6 fatty acids. Typically, forage used in horse feed is higher in the omega-3 fatty acids and using a supplement that is high in omega-6 fatty acids may cause a high pro-inflammatory agent and create problems with the physiology of the horse. The omega-3 fatty acids typically include Eicosapentaenoic acid (EPA) and Docosahexaenoic acid (DHA). Some prior art techniques used to supplement a horse's diet have taken flax seed and used the flax seeds as a top dressing on the horse feed. These flax seeds, however, are not ground by the horse's teeth and as a result, the effectiveness of the flax seed is reduced and is not that effective. Some horse owners may grind the flax seed in a mill prior to feeding the horse, but the ground flax seed becomes rancid quickly since it is not a stabilized, milled flax seed. Even a container of commercially prepared ground flax seed, once it is not refrigerated, may go rancid quickly.

Also, it is difficult to gauge the amount of fat that the horse will receive when using any flax seed product. A horse's total diet should include no more than 15% fat. Diets that exceed that limit could have a negative impact on fermentation in the horse's hind gut. Undigested fat passes from the small intestine to the horse's hind gut where it alters the microbial balance required for digesting the cellulose in plant material. As a result, the horse may change its dietary patterns and go off its feed and obtain diarrhea, which counters the effect of any horse feed the horse is fed.

The LA belongs to the omega-6 family and the ALA belongs to the omega-3 family of fatty acids. It has been found that the horse feed dietary supplement composition, in accordance with a present example as described, is an effective horse feed dietary supplement composition high in the omega-3 family of fatty acids and is shelf stable for up to two years. It will not go rancid when placed in storage either in a refrigerator or even for periods of time in a barn near the horses. It has an excellent omega-3 content and is an advantageous top dressing to the horse feed. In one example, about 0.5 to about 1.5% by weight of the horse feed dietary supplement composition is top dressed to the horse feed based upon the weight of total horse feed fed to the horse on a daily basis. In one example, a 1% weight of the horse feed dietary supplement composition has been found effective as a top dressing to the horse feed based upon an 1,100 pound horse. In another example, the horse feed was top dressed with the horse feed dietary supplement composition using about 2 ounces of the partially defatted seed mill composition, once in the morning and once in the evening.

The flour may be about 30-40% insoluble fiber in one example and 48-60% insoluble fiber in another example or be in the range of 30-60% in other examples. In a specific example used with the horse feeding study, the horse feed dietary supplement composition was about 56% fiber and provided a high level of omega-3 alpha linolenic acid (ALA). For example, after supercritical carbon dioxide extraction forming the final composition, the fat had been reduced to 6% in one example and protein increased to about 30%. The ALA to LA native seed oil may also be formed of about 5-8%.

An advantageous aspect of the horse feed dietary supplement composition is the flour forming the composition exhibits pH dependent thixotropic properties when mixed with water. This is also enhanced by the addition of the fructo-oligosaccharides, and in one example, about 2 to about 3% fructo-oligosaccharides. The horse feed dietary supplement composition has a high ORAC, i.e., as high as 11,200, which is an expectedly high value and results from carefully prepared chia before extraction and supercritical carbon dioxide processing parameters.

This horse feed dietary supplement composition was well received as a supplement by the horses without rejection on the feeding study explained below. This supplement dress fed on the horse feed was not rejected by the horses, as some prior art supplement feeds had been rejected as reported in some literature.

A horse feed study using the horse feed dietary supplement composition was conducted to evaluate the effect of the horse feed dietary supplement composition corresponding to the modified ChiaMax® on the general health and well-being of both event and dressage horses. The horse feed dietary supplement composition as described above is a partially defatted chia (*Salvia hispanica* L.) seed meal rich in protein, fiber, minerals and omega-3 fatty acids. Whole chia seed contains about 32% fat and 21% protein. By extracting the seed with the relatively pure supercritical carbon dioxide as described above, the composition is improved and the fat is reduced to 6% and protein increased to 30% in one non-limiting example. The horse feed dietary supplement composition in this example also contains 56% fiber and provides a high level of omega-3 alpha-linolenic acid.

Horse Study Design: 100 horses in the southeast
  2 ounces (57 g) mixed/top-dressed in feed, twice per day (AM/PM)
  Average age was 13 years, minimum 2, maximum 28
  Average weight was 1,010 pounds, minimum 275, maximum 1,850
  On day 0 and 30, owners were asked to rate the following conditions on a 1-5 scale with 1 representing a poor condition and 5 as excellent: coat condition; digestion; mane condition; insulin resistance; tail condition; hoof growth; and joint/muscle flexibility. Results were obtained from all 100 horses in the study (50 owners). Day 0 and 30 conditions were compared using a Paired t-Test. Insulin resistance was reported by only a few participants and not included in further comparisons. All other conditions showed a significant improvement from the 30 day consumption of the horse feed dietary supplement composition corresponding to the modified and enhanced ChiaMax ($p<0.001$).

| Average Condition Rating | | | |
|---|---|---|---|
| Condition | Day 0 | Day 30 | % Change |
| Coat | 2.4 | 4.1 | 73 |
| Mane | 2.6 | 3.7 | 41 |
| Tail | 2.6 | 3.7 | 41 |
| Hoof | 2.5 | 3.7 | 51 |
| Digestion | 2.9 | 3.8 | 28 |
| Joint | 2.6 | 3.6 | 37 |

In addition to the rated conditions, multiple horse owners also reported specific observations on: diminished insect sensitivity/itching; improved energy; and improved digestion for their horses used in the study. As an example, the horses displayed visible and positive changes in their coat before and after feeding with the horse feed dietary supplement composition as described.

Although a specific horse feed dietary supplement composition that includes 30% protein, 6% wt/wt of the 3.0-3.3:1 mixture of ALA to LA native seed oil and 56% insoluble fiber was used, it should be understood that different ranges of those ingredients and components may be used for the horse feed dietary supplement composition depending on the type of horse. The composition may be applied to different animals and not be limited to horses. The composition was specifically tailored for the use of a horse feed dietary supplement composition, but can be modified or applied using the same or different composition and percentages of ingredients for other animals.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A method of increasing the energy and improving the health and coat of a horse, comprising:
    administering to a horse in need thereof a horse feed comprising an effective amount of a shelf stable, partially defatted supercritical $CO_2$ fluid solvent extracted whole grain flour derived from *Salvia hispanica* L. whole ground seed and that is free of cyanogenic glycosides, vitamin antagonists, and gluten, the flour comprising minerals, about 25% to 35% protein, about 48% to 60% insoluble fiber; about 5% to 8% wt/wt of oil which contains about 1.0-3.3:1 of a mixture of ALA to LA; and an antioxidant.

2. The method of claim 1, wherein said prior to said administering step, the horse feed is added, as a top dressing, to horse feed grain.

3. The method of claim 2, wherein said administering comprises:
    a) administering to said horse, an amount of the horse feed that is about 0.1% by weight of the horse and
    b) wherein administering occurs once in the morning and once in the evening.

4. The method according to claim 1, wherein said administering comprises: administering an amount of the horse feed that is about 0.5 to 1.5% by weight of the horse on a daily basis.

5. The method according to claim 1, wherein the flour comprises about 30% by weight of protein.

6. The method according to claim 1, wherein the flour exhibits pH dependent thixotropic properties when mixed with water.

7. The method according to claim 1, wherein the flour includes fructo-oligosaccharides.

8. The method according to claim 7, wherein the flour comprises about 2-3% of fructo-oligosaccharides.

9. The method of claim 1, wherein the antioxidant comprises rosemary oil, rosemary extract containing 20-40% carnosic acid or carnosic acid.

10. The method according to claim 1, wherein the flour comprises about 30% protein, 6% of the mixture of ALA to LA, and 56% insoluble fiber.

11. The method according to claim 1, wherein the shelf stable, partially defatted supercritical $CO_2$ fluid solvent extracted whole grain flour is made by a process comprising cracking whole chia seed to form a cracked chia seed, adding rosemary oil, rosemary extract containing 20-40% carnosic acid or carnosic acid to the cracked chia seed and subjecting the cracked chia seed to supercritical $CO_2$ extraction at about 200-700 bar at a temperature of about 40 to 80° C.

* * * * *